United States Patent
Ryu et al.

(10) Patent No.: US 7,035,685 B2
(45) Date of Patent: Apr. 25, 2006

(54) APPARATUS AND METHOD FOR MEASURING ELECTROENCEPHALOGRAM

(75) Inventors: Chang-su Ryu, Daejon (KR);
Yoon-seon Song, Daejon (KR);
Seung-chul Shin, Daejon (KR);
Seung-hoon Nam, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 774 days.

(21) Appl. No.: 10/165,628

(22) Filed: Jun. 6, 2002

(65) Prior Publication Data

US 2003/0139683 A1   Jul. 24, 2003

(30) Foreign Application Priority Data

Jan. 22, 2002   (KR) .......................... 2002-3713

(51) Int. Cl.
*A61B 5/04* (2006.01)

(52) U.S. Cl. ................................... 600/544
(58) Field of Classification Search ............... 600/544, 600/545
See application file for complete search history.

(56) References Cited

U.S. PATENT DOCUMENTS

| | | | |
|---|---|---|---|
| 4,408,616 A | * | 10/1983 | Duffy et al. ............... 600/544 |
| 4,550,736 A | | 11/1985 | Broughton et al. |
| 5,513,649 A | | 5/1996 | Gevins et al. |
| 5,649,061 A | | 7/1997 | Smyth |
| 6,115,631 A | * | 9/2000 | Heyrend et al. ............ 600/544 |

* cited by examiner

*Primary Examiner*—Max F. Hindenburg
*Assistant Examiner*—Navin Natnithithadha
(74) *Attorney, Agent, or Firm*—Blakely, Sokoloff, Taylor & Zafman

(57) ABSTRACT

An electroencephalogram measuring apparatus and method. The electroencephalogram measuring method includes detecting electroencephalogram data of an experimentee, amplifying the detected electroencephalogram data, and converting the data into a digital signal. Also, provided is a high-speed Fourier transforming the converted digital electroencephalogram data, calculating an output value for each frequency of the Fourier transformed electroencephalogram, calculating an output value for each frequency of the electroencephalogram for a predetermined time interval and calculating a relative output value for the ground state of the experimentee. Further provided is comparing the calculated relative output value for each frequency for each predetermined time interval for the ground state of the experimentee, with a predetermined value.

8 Claims, 3 Drawing Sheets

(1 of 3 Drawing Sheet(s) Filed in Color)

APPARATUS AND METHOD FOR MEASURING ELECTROENCEPHALOGRAM

BACKGROUND OF THE INVENTION

1. Field of the Invention

The present invention relates to an apparatus for measuring an electroencephalogram and a method for driving the apparatus, and more particularly, to an electroencephalogram (EEG) measuring apparatus for measuring a pure electroencephalogram without combined noise waves, by considering the ground state of an experimentee and a method for driving the apparatus.

2. Description of the Related Art

An electroencephalogram which enables to spatiotemporally recognize the activities of a brain is a leading living body signal, and is widely used in clinical research and brain function researches. Recently, the electroencephalogram is used in bio-feedback in which the mental states of a user is improved through modulation of an electroencephalogram by an external stimulus. Also, using the living body signals such as the electroencephalogram, an eletrocardiogram, or Galvanic Skin Resistance (GSR), the emotion of an individual is evaluated. In addition, the electroencephalogram is applied to a Brain-Computer Interface (BCI) field which aims to achieve a direct interface between humans and machines through an electroencephalogram without using languages or body actions.

However, in measuring a human electroencephalogram, noise waves, including an electromyogram generated by human actions, an electrooculogram generated by eye movement, an electrocardiogram, a slow wave generated by respiration and perspiration, and a signal generated by skin deformation due to an electrode attached for measuring an electroencephalogram, are combined into the electroencephalogram. If this noise waves are combined with the electroencephalogram, the electroencephalogram of an experimentee cannot be accurately measured.

Therefore, a prior art method which removes noise waves combined by human actions is disclosed in U.S. Pat. No. 4,550,736, entitled "Movement artifact detector for sleep analysis". According to the method, in order to remove noise waves combined by actions when a sleeping electroencephalogram is measured, it is determined that noise waves are combined if any one of the following three components is detected, including an electromyogram component (equal to or greater than 30 Hz, 18 µV) which has a greater value than the electroencephalogram, a component (equal to or greater than 30 Hz, −9 µV~9 µV) which is generated when an electroencephalogram amplifier returns to a normal state after data collection is temporarily stopped due to a disorder in the electroencephalogram amplifier, and a noise wave component (equal to or less than 1.2 Hz, equal to or greater than 200 µV) due to respiration or perspiration.

However, the method does not consider the facts that the amplitude of an electroencephalogram changes by individuals, and the frequency component of an electroencephalogram changes differently according to physical and cognitive information processing.

Also, there is a method for removing noise waves generated by actions, using a sensor, but the method needs additional cost.

SUMMARY OF THE INVENTION

To solve the above problems, it is a first objective of the present invention to provide an electroencephalogram measuring apparatus which can remove an electroencephalogram in which noise waves are combined, by considering individual differences, and can output only an electroencephalogram in which no noise waves are combined.

It is a second objective of the present invention to provide an electroencephalogram measuring method by the electroencephalogram measuring apparatus.

To accomplish the first objective of the present invention, there is provided an electroencephalogram measuring apparatus having an electroencephalogram detection unit which detects electroencephalogram data; an electroencephalogram amplifying unit which amplifies the electroencephalogram data measured in the electroencephalogram detection unit; an A/D converting unit which converts the amplified electroencephalogram data from an analog signal to a digital signal; an electroencephalogram processing unit which, using the electroencephalogram data which is converted into a digital signal, outputs an output value for each frequency at each time interval for the ground state of an experimentee, and determines whether or not noise waves are combined with the electroencephalogram; and a display unit which displays the result of the electroencephalogram processing unit.

It is preferable that the electroencephalogram amplifying unit amplifies sensed electroencephalogram data and filter a predetermined frequency band of the data.

It is preferable that the electroencephalogram processing unit has a Fourier transform unit which separates a sine wave from the electroencephalogram data amplified in the electroencephalogram amplifying unit; a data storage unit which stores the electroencephalogram of the ground state of the experimentee; and a control unit which calculates a relative output value for each frequency at each predetermined time interval of the ground state of the experimentee, by using the output value for each frequency of the electroencephalogram obtained by the Fourier transform unit, and the output value for each frequency obtained from the electroencephalogram data of the ground state of the experimentee.

It is preferable that the Fourier transform unit high-speed Fourier transforms the electroencephalogram data.

It is preferable that the data storage unit which stores the electroencephalogram of the ground state stores electroencephalogram data measured in an eye-closed and relaxed state, or in an interval before stimulus.

It is preferable that the control unit has a first calculating unit which calculates an output value for each frequency of the electroencephalogram which is Fourier transformed; a second calculating unit which calculates the size of an output value for each frequency at each predetermined time interval using the output of the first calculating unit; a third calculating unit which calculates a relative output value for each frequency at each predetermined time interval of the ground state, by dividing the output of the second calculating unit by the output value for each frequency of the ground state of the experimentee; and a comparison unit which compares the output of the third calculating unit with a predetermined value.

It is preferable that in the second calculating unit which calculates an output value for each frequency at each predetermined time interval, the time interval overlaps with a preceding time interval and a following time interval.

To accomplish the second objective of the present invention, there is provided an electroencephalogram measuring method includes detecting electroencephalogram data of an experimentee; amplifying the detected electroencephalogram data, and converting the data into a digital signal;

high-speed Fourier transforming the converted digital electroencephalogram data; calculating an output value for each frequency of the Fourier transformed electroencephalogram; calculating an output value for each frequency of the electroencephalogram for a predetermined time interval; calculating a relative output value for the ground state of the experimentee, by dividing the output value for each frequency at each predetermined time interval by the output value for each frequency of the ground state of the corresponding experimentee; and comparing the calculated relative output value for each frequency for each predetermined time interval for the ground state of the experimentee, with a predetermined value, and if the relative output value for each frequency for each predetermined time interval for the ground state of the experimentee is less than the predetermined value, determining that noise waves are not combined with the electroencephalogram, and outputting the electroencephalogram data, and if the relative output value for each frequency for each predetermined time interval for the ground state of the experimentee is greater than the predetermined value, determining that noise waves are combined with electroencephalogram, and not outputting the electroencephalogram data.

BRIEF DESCRIPTION OF THE DRAWINGS

The patent or application file contains at least one drawing executed in color. Copies of this patent or patent application publication with color drawing will be provided by the Office upon request and payment of the necessary fee.

The above objects and advantages of the present invention will become more apparent by describing in detail preferred embodiments thereof with reference to the attached drawings in which.

DESCRIPTION OF THE PREFERRED EMBODIMENTS

Figure 1:
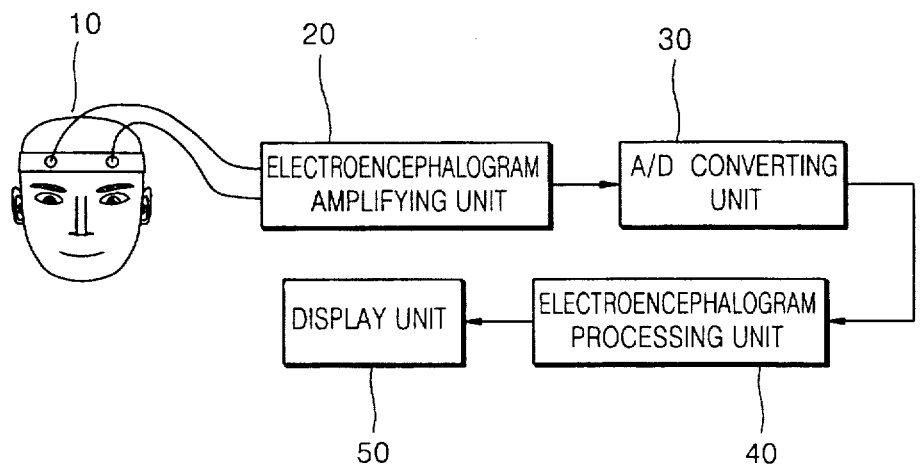
FIG. 1 is a schematic block diagram showing an electroencephalogram measuring apparatus according to the present invention.

Referring to FIG. 1, the electroencephalogram measuring apparatus of the present invention is formed with an electroencephalogram detection unit 10 which detects electroencephalogram data, an electroencephalogram amplifying unit 20 which amplifies the electroencephalogram data measured in the electroencephalogram detection unit 10, an A/D converting unit 30 which converts the amplified electroencephalogram data from an analog signal to a digital signal, an electroencephalogram processing unit 40 and a display unit 50 which displays the result of the electroencephalogram processing unit 40. The electroencephalogram processing unit 40 obtains a relative output value for each frequency each time, using the converted electroencephalogram data and considering the ground state of an experimentee, and determines based on the relative output value whether or not noise waves are combined. If it is determined that noise waves are combined, the electroencephalogram processing unit 40 makes the output of electroencephalogram stop.

Here, the electroencephalogram detection unit 10 is an electrode which measures electroencephalogram data, and the electrode is attached to the forehead of the experimentee and detects electroencephalogram data. At this time, the electrode which is attached to the forehead of the experimentee may be arranged according to a 10–20 International nomenclature, or other methods The electroencephalogram amplifying unit 20 amplifies the electroencephalogram data measured by the electroencephalogram detection unit 10 to a predetermined level as described above. Also, the electroencephalogram data amplified in the electroencephalogram amplifying unit 20 is, for example, 60 Hz band filtered.

Figure 2:
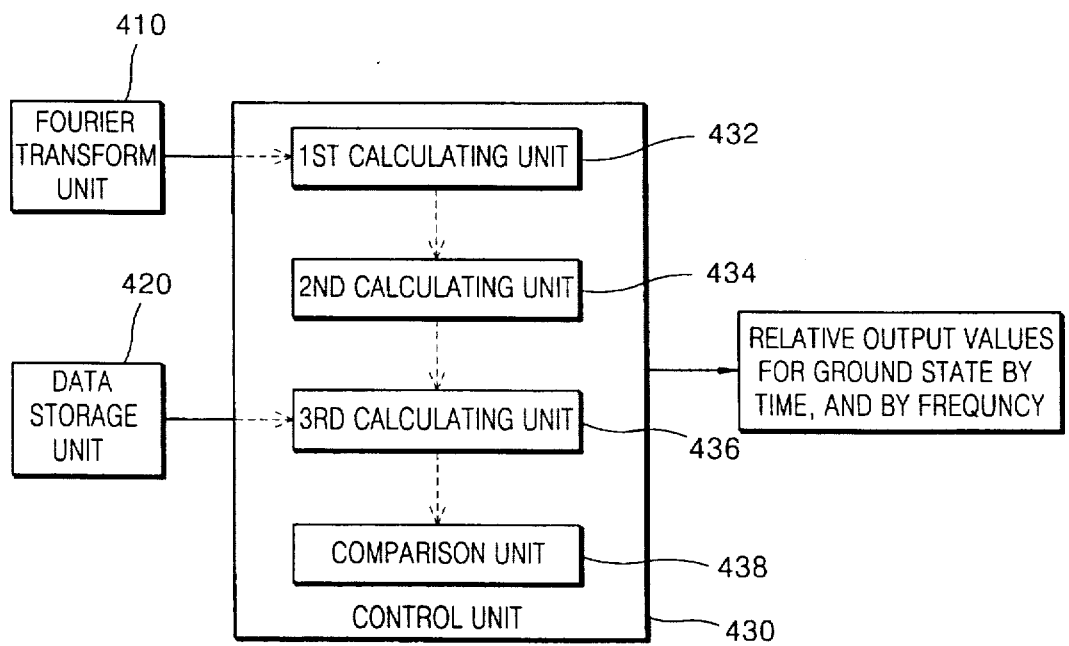
FIG. 2 is a schematic block diagram of the structure of an electroencephalogram processing unit according to the present invention.

Also, the electroencephalogram processing unit 40, as shown in FIG. 2, has a Fourier transform unit 410 which separates a sine wave from the electroencephalogram data which is amplified in the electroencephalogram amplifying unit 20, a data storage unit 420 which stores the electroencephalogram of a ground state of the experimentee, and a control unit 430 which calculates a relative output value for each frequency at each time, considering the ground state of the experimentee, and using the electroencephalogram data converted by the Fourier transform unit 410, and the electroencephalogram data of a ground state of the experimentee.

The Fourier transform unit 410, for example, performs high speed Fourier transform.

The data storage unit 420 which stores the electroencephalogram of a ground state, stores, for example, electroencephalogram data measured in an eye-closed and relaxed state, or in an interval before stimulus.

Also, the control unit 430 has a first calculating unit 432 which calculates an output value for each frequency after Fourier transform, a second calculating unit 434 which calculates an output value for each frequency at each time, by repeatedly performing the operation of the first calculating unit 432, a third calculating unit 436 which outputs a relative output for each frequency at each time considering the ground state after dividing the outputs of the second calculating unit 434 by outputs for each frequency of the ground state of each experimentee, and a comparison unit 438 which compares the output of the third calculating unit 436 with a predetermined value.

The first calculating unit 432 calculates the size of the absolute value $(a^2+b^2)$ of the integer part and the imaginary number part (a+bi) from the Fourier transform unit 410, that is, the output value.

The second calculating unit 434 repeatedly performs the operation of the first calculating unit 432 at each time interval, and calculates the output value for each frequency at each predetermined time interval. At this time, the time interval may be, for example, 0.375 seconds, and about 91.7% of the time interval may overlap with a preceding time interval or a following time interval.

The third calculating unit 436 divides the output value for each frequency at each time interval obtained in the second calculating unit 434, by the output value for each frequency for electroencephalogram data of the ground state of each experimentee. Thus, the relative output value for each frequency at each time interval considering the ground state can be obtained.

The comparison unit 438 compares the relative output value (the output of the third calculating unit 436) for each frequency at each time interval considering the ground state of each experimentee with a predetermined value. At this time, the predetermined value is roughly 3, and if the relative output value is equal to or less than the predetermined value, it is determined that noise waves are not combined with the electroencephalogram. Meanwhile, if the relative output value is greater than 3, it is regarded that noise waves are combined with the electroencephalogram, and the output of electroencephalogram data is stopped.

Figure 4:
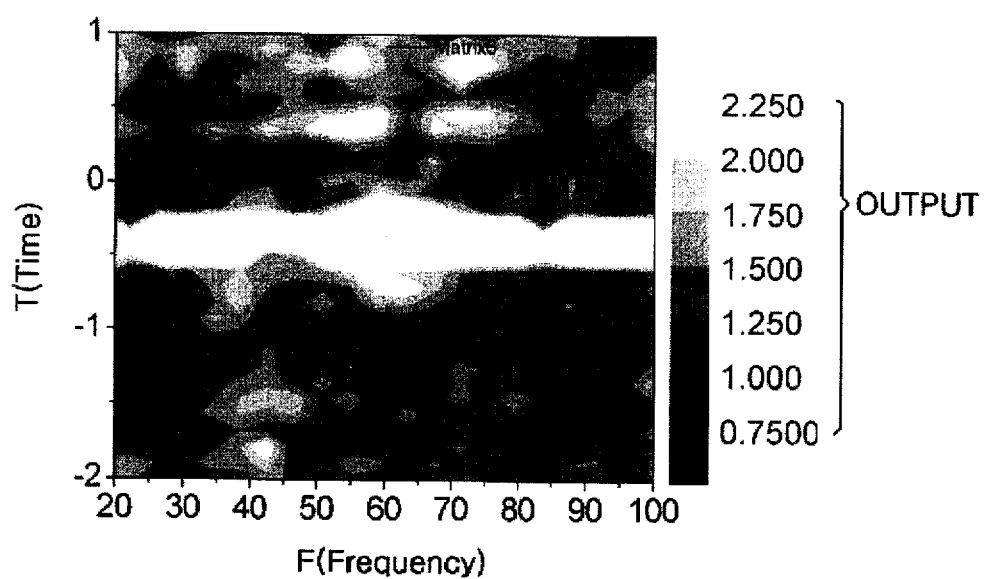
FIG. 4 is a photo showing the result of processing an electroencephalogram according to the present invention.

The display unit 50, as shown in FIG. 4, illustrates the size of the relative output value for each frequency at each time interval, using different colors.

An electroencephalogram method using the electroencephalogram measuring apparatus of the present invention will now be explained.

Figure 3:
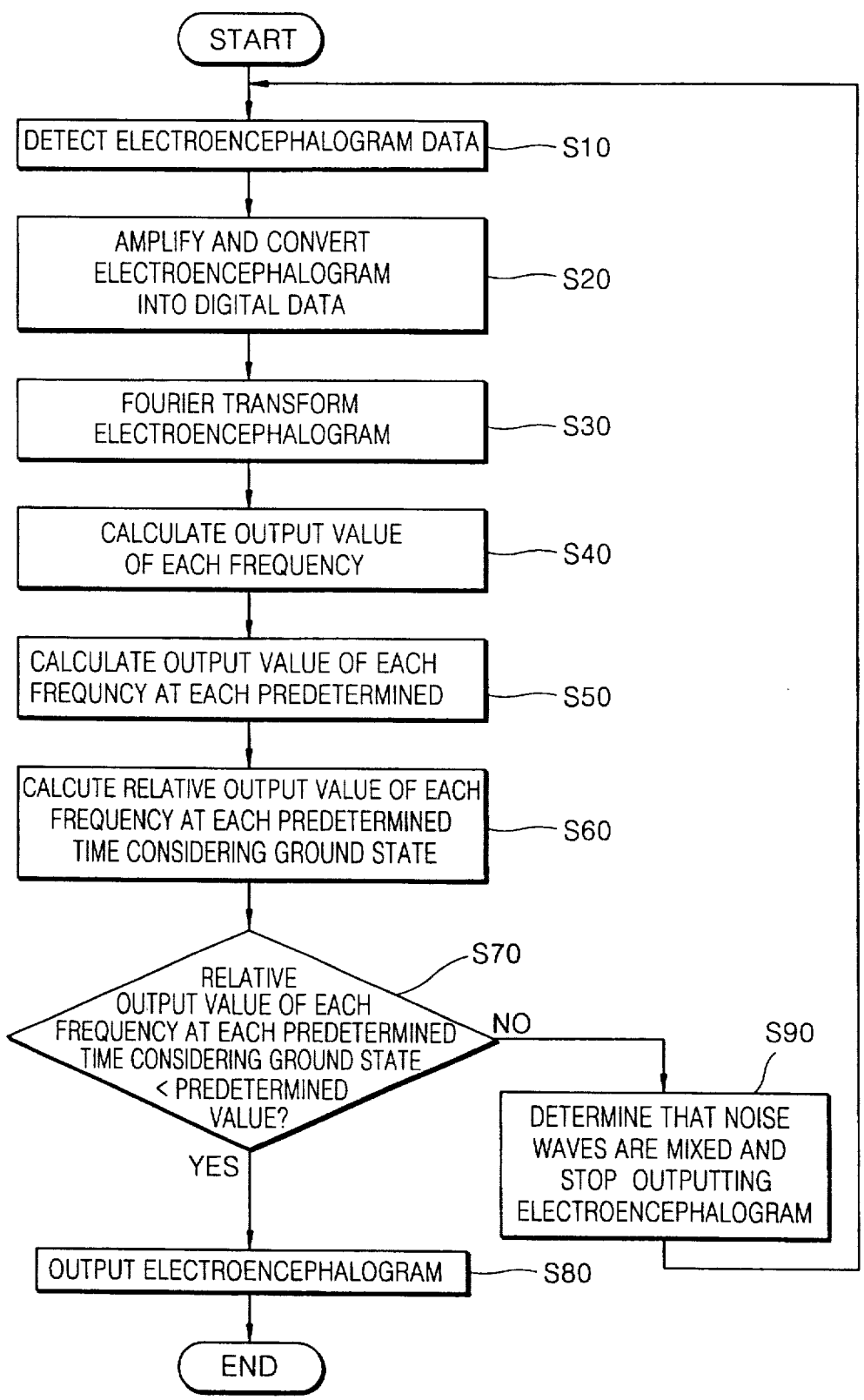
FIG. 3 is a flowchart for explaining the operation of an electroencephalogram measuring apparatus according to the present invention.

Referring to FIG. 3, first, electroencephalogram data is detected in the electroencephalogram detection unit in step S10.

Then, the electroencephalogram data is amplified in the electroencephalogram amplifying unit 20, and is converted into a digital signal in the A/D converting unit 30 in step S20. At this time, in amplifying electroencephalogram data, a predetermined frequency band can be filtered.

The electroencephalogram data which is converted into a digital signal is high speed Fourier transformed in the Fourier transform unit 410 of the electroencephalogram processing unit 40 in step S30.

Next, the first calculating unit 432 of the control unit 430 of the electroencephalogram processing unit 40 calculates an output value, which is the sum of the squares of the integer value and imaginary number that are Fourier transformed, for each frequency in step S40.

Then, the second calculating unit 434 calculates the output value for each frequency at each predetermined time interval in step S50.

Then, by dividing the output value for each frequency at each predetermined time interval by the output value for each frequency of the ground state of a corresponding experimentee, the relative output value for each frequency at each predetermined time interval considering the ground state of the experimentee is calculated in step S60.

Next, the relative output value for each frequency at each predetermined time interval considering the ground state of the experimentee is compared with a predetermined value in step S70. Here, if the relative output value for each frequency at each predetermined time interval considering the ground state of the experimentee is less than the predetermined value, it is determined that noise waves are not combined with the electroencephalogram, and the electroencephalogram data is output in step S80. Meanwhile, if the relative output value for each frequency at each predetermined time interval considering the ground state of the experimentee is greater than the predetermined value, it is determined that noise waves are combined with the electroencephalogram, and the electroencephalogram data is not output in step S90, and a step for detecting new electroencephalogram data is performed.

Thus, according to the present invention, an electroencephalogram output value for each frequency at each predetermined time interval is calculated, and the output value is divided by the output value for each frequency of the ground state of a corresponding experimentee so that the relative output value for each frequency at each time interval considering the ground state of the experimentee is obtained. Then, the relative output value for each frequency at each time interval considering the ground state of the experimentee is compared with a predetermined value, and only when noise waves are not combined with the electroencephalogram, the electroencephalogram data is output.

As described above in detail, according to the present invention, the frequency component of an electroencephalogram is analyzed at each time interval, and from this, a relative result for the ground state of each experimentee can be obtained. According to this, even when the amplitudes of an electroencephalogram differs for each experimentee, or when the frequency component shows different changes according to the physical, cognitive information processing, the electroencephalogram with which noise waves are combined can be removed.

Also, additional costs for additional devices such as a separate sensor for removing noise waves are not needed.

So far, optimum embodiments are explained in the drawings and specification, and though specific terminologies are used here, those were only to explain the present invention. Therefore, the present invention is not restricted to the above-described embodiments and many variations are possible within the spirit and scope of the present invention.

What is claimed is:

1. An electroencephalogram measuring apparatus comprising:
   an electroencephalogram detection unit which detects electroencephalogram data;
   an electroencephalogram amplifying unit which amplifies the electroencephalogram data measured in the electroencephalogram detection unit;
   an A/D converting unit which converts the amplified electroencephalogram data from an analog signal to a digital signal;
   an electroencephalogram processing unit which, using the electroencephalogram data which is converted into a digital signal, outputs an output value for each frequency at each time interval for the ground state of an experimentee, and determines whether or not noise waves are combined with the electroencephalogram; and
   a display unit which displays the result of the electroencephalogram processing unit.

2. The apparatus of claim 1, wherein the electroencephalogram amplifying unit amplifies sensed electroencephalogram data and filter a predetermined frequency band of the data.

3. The apparatus of claim 1, wherein the electroencephalogram processing unit comprises:
   a Fourier transform unit which separates a sine wave from the electroencephalogram data amplified in the electroencephalogram amplifying unit;
   a data storage unit which stores the electroencephalogram of the ground state of the experimentee; and
   a control unit which calculates a relative output value for each frequency at each predetermined time interval of the ground state of the experimentee, by using the output value for each frequency of the electroencephalogram obtained by the Fourier transform unit, and the output value for each frequency obtained from the electroencephalogram data of the ground state of the experimentee.

4. The apparatus of claim 3, wherein the Fourier transform unit high-speed Fourier transforms the electroencephalogram data.

5. The apparatus of claim 3, wherein the data storage unit which stores the electroencephalogram of the ground state stores electroencephalogram data measured in an eye-closed and relaxed state, or in an interval before stimulus.

6. The apparatus of claim 3, wherein the control unit comprises:

a first calculating unit which calculates an output value for each frequency of the electroencephalogram which is Fourier transformed;

a second calculating unit which calculates the size of an output value for each frequency at each predetermined time interval using the output of the first calculating unit;

a third calculating unit which calculates a relative output value for each frequency at each predetermined time interval of the ground state, by dividing the output of the second calculating unit by the output value for each frequency of the ground state of the experimentee; and a comparison unit which compares the output of the third calculating unit with a predetermined value.

7. The apparatus of claim 6, wherein in the second calculating unit which calculates an output value for each frequency at each predetermined time interval, the time interval overlaps with a preceding time interval and a following time interval.

8. An electroencephalogram measuring method comprising:

detecting the electroencephalogram data of an experimentee;

amplifying the detected electroencephalogram data, and converting the data into a digital signal;

high-speed Fourier transforming the converted digital electroencephalogram data;

calculating an output value for each frequency of the Fourier transformed electroencephalogram;

calculating an output value for each frequency of the electroencephalogram for a predetermined time interval;

calculating a relative output value for the ground state of the experimentee, by dividing the output value for each frequency at each predetermined time interval by the output value for each frequency of the ground state of the corresponding experimentee; and comparing the calculated relative output value for each frequency for each predetermined time interval for the ground state of the experimentee, with a predetermined value, and if the relative output value for each frequency for each predetermined time interval for the ground state of the experimentee is less than the predetermined value, determining that noise waves are not combined with the electroencephalogram, and outputting the electroencephalogram data, and if the relative output value for each frequency for each predetermined time interval for the ground state of the experimentee is greater than the predetermined value, determining that noise waves are combined with electroencephalogram, and not outputting the electroencephalogram data.

* * * * *